United States Patent [19]

Kotyk et al.

[11] Patent Number: 4,825,146

[45] Date of Patent: Apr. 25, 1989

[54] UNTHRESHED HEAD GRAIN LOSS MONITOR

[75] Inventors: Wayne M. Kotyk; Thomas G. Kirk; Robert J. Wilson; James N. Wilson, all of Saskatchewan, Canada

[73] Assignee: Canadian Patents & Development Limited, Ottawa, Canada

[21] Appl. No.: 190,240

[22] Filed: May 4, 1988

[30] Foreign Application Priority Data

May 15, 1987 [CA] Canada ................................. 537329

[51] Int. Cl.$^4$ ............................................ G01R 27/00
[52] U.S. Cl. ................................ 324/58.5 B; 73/861; 56/102; 56/DIG. 15
[58] Field of Search ................... 73/198, 861; 56/10.2, 56/DIG. 2, DIG. 15; 324/58.5 A, 58.5 B

[56] References Cited

U.S. PATENT DOCUMENTS

| | | | |
|---|---|---|---|
| 4,239,010 | 12/1980 | Amburn | 324/58.5 A X |
| 4,336,611 | 7/1982 | Mailander | 56/DIG. 15 X |
| 4,765,190 | 8/1988 | Strubbe | 56/DIG. 15 |

Primary Examiner—Herbert Goldstein
Attorney, Agent, or Firm—Ronald G. Bitner

[57] ABSTRACT

A device for indicating grain loss resulting from unthreshed heads in a combine harvester using a microwave transmitter-sensor. The device provides an output signal whose magnitude is a function of the mass of passing effluent which when compared to that of a typical threshed head provides a measure of unthreshed head grain loss.

The device further provides that the output signal for unthreshed heads is distinct from that of loose grain providing means of distinguishing unthreshed head grain loss and loose grain loss.

5 Claims, 2 Drawing Sheets

UNTHRESHED HEAD GRAIN LOSS MONITOR

FIELD OF THE INVENTION

This invention relates to an apparatus for indicating grain loss in unthreshed heads in a combine harvester.

BACKGROUND OF THE INVENTION

The loss of grain from a combine harvester due to unthreshed heads, i.e. grain loss resulting from grain kernels not being threshed from the heads, is related largely to the cylinder to concave clearance and the cylinder speed. Crop variables such as crop variety, crop moisture content and machine loading also affect these losses and complicate making the adjustments for minimizing the losses.

One of the difficulties is the detection and measurement of losses due to unthreshed heads that is taking place. There is presently no entirely satisfactory method of measuring such losses. Conventional grain loss monitors will detect loose kernels of grain but will not detect kernels remaining in the heads. An example of a grain loss monitor utilizing acoustic-electric sensing is disclosed in U.S. Pat. No. 4,004,289.

The procedure most frequently used by combine operators to determine unthreshed head loss is to visually inspect the heads that have passed through the combine for unthreshed and make the adjustments considered to be appropriate.

Another method presently used involves collecting the effluent from the combine in a recepticle. The effluent is first run through a cleaning system to separate the loose grain and is then rethreshed. After the rethreshing, which separates the kernels from the heads, the material is again passed through a cleaning system to isolate the loose grain which represents the grain loss from the unthreshed heads. Although this method provides a quantitative measure, it does not provide a continuous or instantaneous measure, and may not provide a measure that is representative of the entire field due to variations in the crop conditions in different locations of the field. This latter method is also expensive and time consuming.

The detection and counting of seeds utilizing microwave transmitter-sensors is known. Examples of such devices are disclosed in U.S. Pat. Nos. 4,239,010 and 4,246,469. These devices operate by providing an output in response to a disturbance in the microwave standing wave pattern generated by passing seeds.

SUMMARY OF THE INVENTION

An object of the present invention is to provide a device that indicates grain loss in unthreshed (incompletely threshed) heads in a combine harvester.

It has been found that grain loss in unthreshed heads can be detected and measured using a microwave transmitter-sensor and based on the principle that a difference in mass exists between a completely threshed, or empty head, and a head having one or more grain kernels.

It has further been found that the device can be made to distinguish between grain in unthreshed heads and loose grain, by an arrangement that provides a different output signal for grain in a head and for loose grain.

The present invention provides an apparatus for measuring grain loss in unthreshed heads in a combine harvester comprising: means for receiving a sample of the harvester effluent and conveying to a detection region; the detection region including a detection surface over which the sample passes; and microwave transmitter-sensor means having a predetermined microwave field pattern and positioned at the detection region such that the traversing of effluent across the detection region produces a disturbance in the microwave field pattern, and wherein said transmitter-sensor means produces a first output signal in response to the disturbance and related in magnitude to the mass of effluent traversing the detector region at a distance spaced from the detection surface, and indicator means responsive to an output signal greater than a predetermined threshold value representative of a threshed head to provide a measure of grain loss in unthreshed heads.

DESCRIPTION OF THE PREFERRED EMBODIMENT

Figure 1:
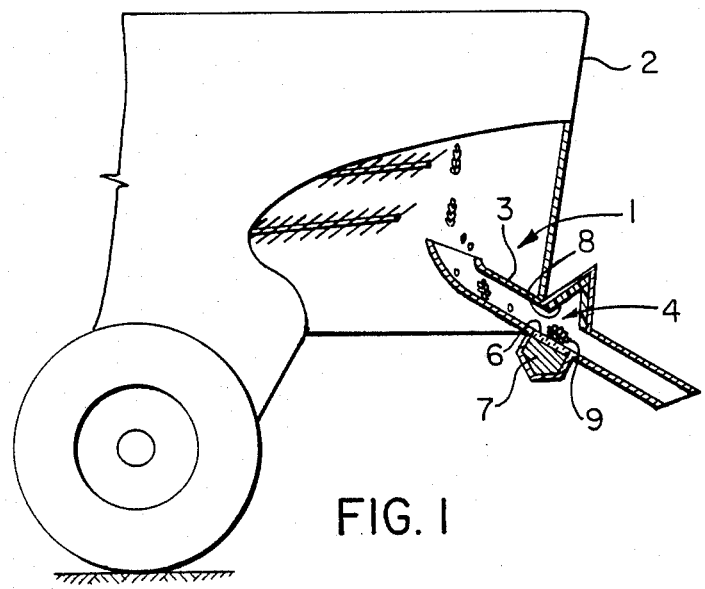
FIG. 1 is a schematic representation of one embodiment of the present invention in combination with a combine harvester.

Referring to FIG. 1, the apparatus includes means 1 for receiving a sample of effluent from a combine harvester 2. The sample is conveyed through passageway 3 to a detection region 4. The detection region 4 includes a window transparent to microwave radiation that defines a detection surface 6 over which the effluent passes.

Microwave transmitter-sensor means 7, is positioned at the detection region 4, providing an output signal in response to a disturbance in the microwave field pattern produced by effluent 9 traversing detection surface 6. A microwave absorber 8 is positioned on the opposite side of passageway 3 to avoid undesirable reflections.

In one embodiment of the present invention the microwave transmitter-sensor means is in the form of a microwave Doppler module that operates with a predetermined frequency and is aligned relative to the detection surface 6 such that the microwave field pattern has a phase polarity relative to the detection surface and effluent as shown in FIG. 2.

Figure 2A:
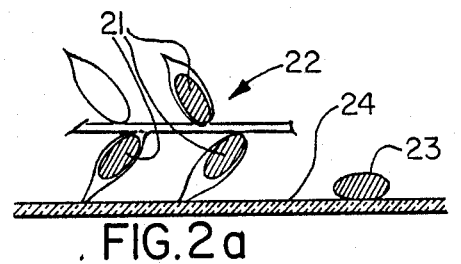
FIG. 2 is a schematic illustration showing the relationship of the position of elements of effluent with respect to the surface in the detection region (2a) and the corresponding microwave field pattern (2b) in one embodiment of the invention.
Figure 2B:
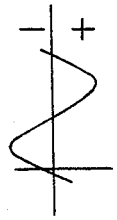

With reference to FIG. 2(a), it can be seen that the position of grain kernels 21 in heads 22 will pass at a different position relative to the detection surface 24 than does loose grain 23. The position relative to the surface corresponds to a particular position in the microwave field pattern of the transmitter-sensor as represented by FIG. 2(b). Specifically, as shown, grain kernels 21 in heads are generally disposed in a region of positive phase polarity while loose grain is disposed in the region of negative polarity.

The output signal from the microwave transmitter-sensor is derived from the disturbance in the microwave field pattern produced by passing effluent. The magnitude of the output signal is proportional to the mass within the sampling volume.

Figures 3A, 3B, 3C:
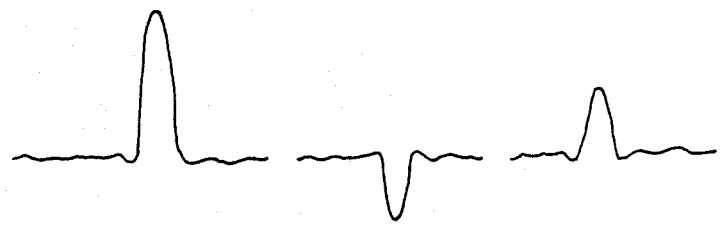
FIG. 3 illustrates typical signals obtained from grain in unthreshed heads 3(a), loose grain 3(b), and threshed head 3(c) in one embodiment of the invention.

FIG. 3 shows traces of the output as obtained from effluent of three different types. Specifically, the output trace of 3(a) corresponds to an unthreshed head containing 2 grain kernels, trace 3(b) corresponds to a loose kernel, and FIG. 3(c) shows a trace corresponding to a completely threshed head containing no grain.

It can be seen that the amplitude of the signal for a head containing grain, FIG. 3(a), is greater than the signal for a completely threshed head containing no grain, FIG. 3(c), due to the larger mass. Hence, a signal with amplitude greater than that produced by a typical empty head can be utilized to indicate the presence of grain in the effluent.

By comparing the output signal with a predetermined value typical of a threshed head containing no grain, discrimination between unthreshed heads and threshed heads can be made. Furthermore, the number of kernels can be estimated from the difference over the typical threshed head signal by computation involving the signal increase for each additional kernel of grain.

With reference to FIGS. 2 and 3, both threshed heads and unthreshed head will typically provide a signal having predetermined phase polarity (positive) due to the position of the center of mass relative to the surface 24. Similarly, loose grain will produce a signal having the opposite (negative) polarity.

Hence, utilizing both the amplitude and polarity of the output signal a determination can be made as to the nature and magnitude of components of the effluent, and particularly, the grain remaining in unthreshed heads and loose grain in the effluent.

The amplitude and polarity of the output signal is related to the net amount of mass above or below a zero phase distance as follows:

$$E = \int_{x=0}^{x=3\pi/w} M(\sin\omega x)dx \quad \omega = 2\pi/z$$

where M is the mass, z is the zero phase distance above the detection surface, and x is the distance of the center of mass from the window surface.

In a device designed for a wheat crop, and using a 10.525 GHz microwave transmitter-sensor, a suitable zero phase distance (z) was found to be about 0.5 cm from the surface and the peak response distance at about 0.75 cm from the surface. This peak response distance is greater than the distance of the centre of mass of a typical stationary wheat head (0.65 cm) in order to compensate for bouncing and interaction of the effluent in operation. The detection region was designed to respond to a single head at a time. The sampling distance was a circle 2.7 cm in diameter and capable of summing a length of head approximately 2 cm in length.

It will be understood that there will be variations in the size, shape, and mass of various components of the effluent for a particular crop and which will not all follow a consistent path across the detection surface, and that therefore the information in the output signal is statistical in nature. Furthermore, it can be seen that different crop types may require adjustment or compensation to obtain an accurate quantitative measurement. For example, a crop material having a different head size may require adjustment of the position of the microwave transmitter-sensor relative to the detection surface. The phase-distance relationship can be altered by changing the oscillator frequency.

Although the embodiment detailed above utilizes a difference in phase polarity for distinguishing between unthreshed head grain loss and loose grain loss, alternate means may be utilized to determine the position relative to the surface of traversing effluent. The alternate means may include any suitable sensing means that provides sensitivity to distance from the detection surface, for example, with the use of a pair of microwave strips one sensitive to mass near the surface representing loose grain and the other sensitive to mass spaced from the surface representing grain in unthreshed heads.

Additional means may be provided to ensure that the effluent traverses the detection region in an orderly and consistent manner, and particularly for directing all components of the effluent onto the detection surface. The means may include a resilient belt positioned above the detection surface, or the use of a curved detector surface such that effluent is directed onto the surface by centripetal force.

Figure 4:
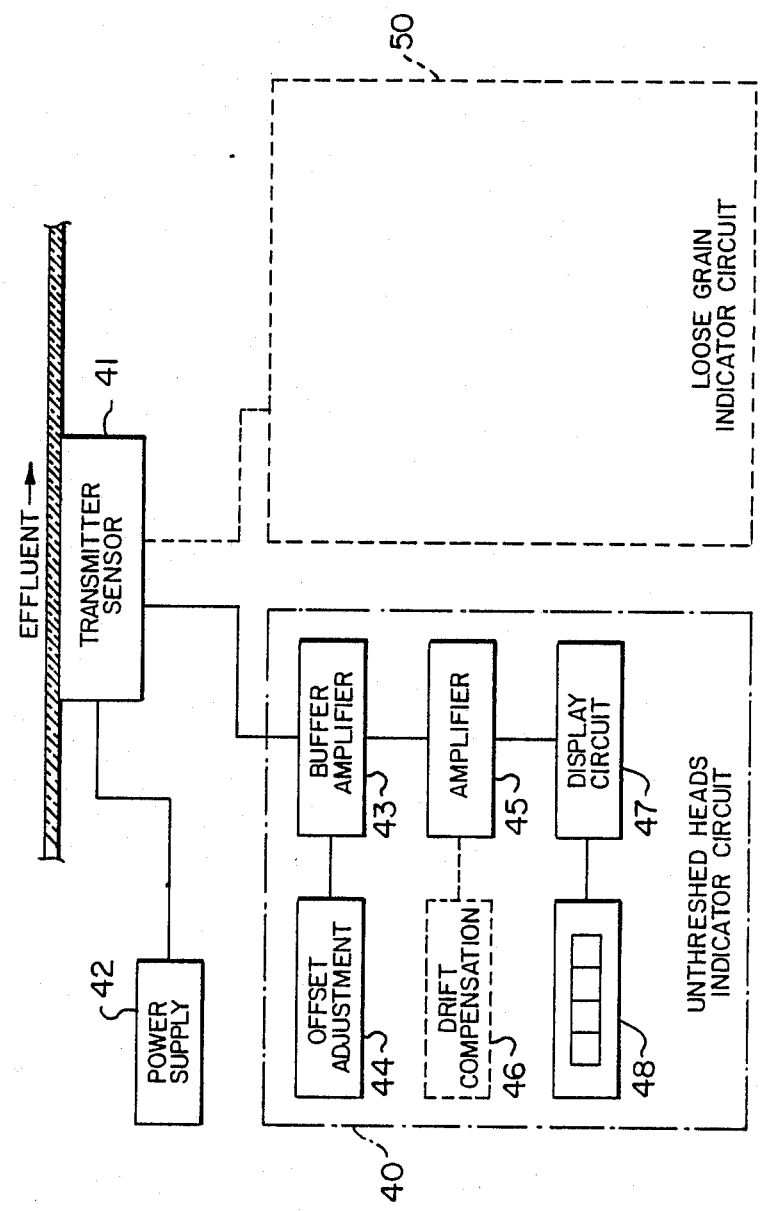
FIG. 4 is a schematic diagram showing one embodiment of the electronic circuit for the present invention.

Referring to FIG. 4, the microwave transmitter-sensor 41 is driven by a suitable power source 42. The unthreshed head indicator circuit 40 includes a buffer amplifier 43 that prevents loading (distortion of) the signal output from the receiver portion of the microwave transmitter-sensor 41. Offset adjustment means 44 permits the zero reference of the output to amplifier 46 to be adjusted. An optional drift compensation circuit 47 may be used to permit the empty output level of amplifier 43 to be stored and subtracted from the signal to amplifier 45.

A display circuit 47 may be used to convert the amplified signal to a digital output for the display 48.

For an indication of loose grain loss, a second indicator circuit 50 would be required that is responsive to a second signal from the transmitter-sensor means 41. The second signal may be provided by the same transmitter-sensor as for the unthreshed head loss indicator, using the opposite phase polarity component of the signal, as detailed above, or alternatively a second transmitter-sensor may be used that is adapted to be sensitive to mass near the surface.

A sensor that measures an operating condition such as harvester speed or harvested grain flow may be used in conjunction with the present invention such that indicators 40 and 50 provide an indication of grain loss per unit area or per unit of threshed grain.

We claim:

1. An apparatus for measuring grain loss in unthreshed heads in a combine harvester comprising:
   means for receiving a sample of the harvester effluent and conveying to a detection region;
   said detection region including a detector surface over which the sample passes;
   microwave transmitter-sensor means operative to generate a microwave field pattern with respect to the detection region such that the traversing of effluent across the detection region produces a disturbance in said microwave field pattern, and wherein said transmitter-sensor means produces a first output signal in response to the disturbance and related in magnitude to the mass of effluent traversing the detector region at a distance spaced from the detection surface, and indicator means responsive to an output signal greater than a predetermined threshold value representative of a threshed head to provide a measure of the grain loss in unthreshed heads.

2. The apparatus of claim 1 wherein said transmitter-sensor means provides a second output signal related to the mass of effluent traversing the detector region near the detection surface, and indicator means responsive to the amplitude of the second output signal to provide an indication of the loose grain loss.

3. The apparatus of claim 2 wherein the microwave transmitter-sensor means has a predetermined wavelength and is positioned relative to the detector surface such that the first and second signals are provided by signal components having opposite phase polarity.

4. The apparatus of claim 1, wherein the detection region is adapted to respond to a single head at a time.

5. The apparatus of claim 1, including means to direct the effluent onto said detection surface.

* * * * *